United States Patent [19]

Herz

[11] 3,962,347

[45] June 8, 1976

[54] HYDROXYSUBSTITUTED POLYMETHYLOXANONANE

[75] Inventor: Kurt S. Herz, Perstorp, Sweden

[73] Assignee: Perstorp AB, Perstorp, Sweden

[22] Filed: Oct. 16, 1973

[21] Appl. No.: 406,935

[30] Foreign Application Priority Data

Nov. 23, 1972 Sweden.............................. 15248/72

[52] U.S. Cl.............................. 260/615 R; 260/410; 260/615 B; 260/DIG. 15; 260/DIG. 24; 252/52 R; 252/55 A; 252/56 R; 252/351; 149/88

[51] Int. Cl.$^2$.......................................... C07L 41/12

[58] Field of Search.................................. 260/615 R

[56] References Cited

UNITED STATES PATENTS

| | | | |
|---|---|---|---|
| 3,658,919 | 4/1972 | Daniel............................. | 260/615 R |
| 3,740,322 | 6/1973 | Wada et al...................... | 260/615 R |
| 3,776,963 | 12/1973 | Zey et al......................... | 260/615 R |

FOREIGN PATENTS OR APPLICATIONS

| | | | |
|---|---|---|---|
| 574,428 | 4/1959 | Canada........................... | 260/615 R |
| 4,427,562 | 11/1969 | Japan.............................. | 260/615 R |

*Primary Examiner*—Howard T. Mars
*Attorney, Agent, or Firm*—Stevens, Davis, Miller & Mosher

[57] ABSTRACT

Method at recovery of pure 3,3,7,7-tetrahydroxymethyl-5-oxanonane from a distillation residue obtained at the production of trimethylolpropane, wherein the 3,3,7,7-tetrahydroxymethyl-5-oxanonane is crystallized by a simple crystallization from a salt containing aqueous solution of the distillation residue having a specially favorable salt proportion.

2 Claims, No Drawings

HYDROXYSUBSTITUTED POLYMETHYLOXANONANE

The present invention relates to a method for the recovery of pure 3,3,7,7-tetrahydroxymethyl-5-oxanonane, below abbreviated THMO. Sometimes the substance is called ditrimethylolpropane.

Trimethylolpropane is produced by the reaction in an aqueous medium of formaldehyde and n-butyraldehyde in the presence of an alkaline catalyst, for example the hydroxide of an alkali metal or an alkaline earth metal. This reaction may be represented as follows:

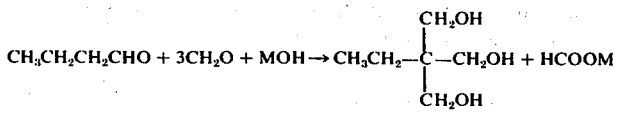

where M represents an alkali metal or alkaline earth metal. This method is very well known in the art. There are many patents and other literature dealing therewith, so that it need not be described in detail.

It is also known before that THMO having the formula

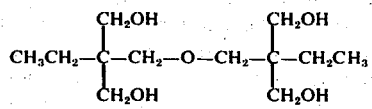

is formed as a by-product at the production of trimethylolpropane. In this connection reference may be made for example to U.S. Pat. No. 3,097,245.

In the industrial production of trimethylolpropane, n-butyraldehyde is reacted with formaldehyde in an aqueous solution in the presence of an alkaline catalyst. After the reaction, trimethylolpropane is separated in a usual manner. Thus, after or without an evaporation, the reaction mixture is subjected to extraction with a solvent, for example ethyl acetate, amyl alcohol, methyl isobutyl ketone, hexyl alcohol, isooctyl alcohol or cyclohexanol. In this way a solution of trimethylolpropane substantially free from formate is obtained. Alternatively, water is substantially removed from the reaction mixture, whereupon the concentrate is filtered while hot to separate formate from crude trimethylolpropane.

The crude trimethylolpropane obtained can be purified direct by vacuum distillation. However, before the vacuum distillation the product can instead be purified from salt by passing it in the form of an aqueous solution through an ion exchanger. By removing the salt, the subsequent vacuum distillation is facilitated and the risk of thermal decomposition of the trimethylolpropane is decreased. By the process described above pure trimethylolpropane is obtained.

In the process according to the present invention one starts with the bottom residue left after said vacuum distillation. In addition to THMO this bottom residue contains different by-products which are non-crystalline at room temperature. Usually the proportion of trimethylolpropane in the residue is 10 – 70 %, normally 30 – 60 %. The content of THMO is usually 10 – 60 %, normally 15 – 50 %. Cyclic and linear formals constitute the rest of organic components in the mixture.

Moreover, the distillation residue contains alkali formate. The amount of formate can vary within wide limits depending on the kind of process used for the production of the trimethylolpropane. In processes including a salt removing step the formate content is usually 0.1 – 5 %. In other kinds of processes the formate content is 5 – 50 %.

In the British Pat. No. 1,291,335 it is mentioned that THMO can be obtained from the distillation residue by crystallization after dissolution in organic solvents or water. However, it is pointed out in said patent that repeated recrystallizations are required to obtain a product having the necessary purity for use as industrial material. However, now it has surprisingly turned out to be possible to simplify said process considerably.

Thus, according to the present invention one has brought about a method for recovery of pure 3,3,7,7-tetrahydroxymethyl-5-oxanonane from a distillation residue obtained at the production of trimethylolpropane. The method is characterized in that the 3,3,7,7-tetrahydroxymethyl-5-oxanonane is crystallized by a simple crystallization from a salt containing aqueous solution of the distillation residue having a specially favourable salt proportion.

Sometimes the salt content of the distillation residue is high enough to make it possible to precipitate crystals of THMO in a satisfactory way after dissolution with water. However, if the salt content of the distillation residue is unsufficient, salt must be added to the aqueous solution of the distillation residue.

The salt in the aqueous solution should be of such a kind that it is completely dissolvabe in water in the temperature and concentration conditions existing at the crystallization process.

One or several different salts of alkali metals or alkaline earth metals with simple organic or inorganic acids can be used in the aqueous solution. These salts can be exemplified by sodium chloride, sodium sulphate, potassium chloride, potassium formate and calcium formate. However, many other salts can be used.

In the usual methods for the production of trimethylolpropane large quantities of sodium formate are obtained. Therefore it is especially suitable to use this salt for said purpose.

If sodium formate constitutes the main part of the salt in the aqueous solution, the salt content ought to amount to 1 – 20 %, preferably 2 – 10 %, calculated upon the weight of the whole solution.

By adjusting the salt concentration of the aqueous solution on a favourable level according to the present invention such conditions can be achieved that a product having a satisfactory purity can be obtained already after the first crystallization. At a demand for a very high purity of the product, this can be brought about after only one recrystallization.

In the method according to the invention said bottom residue is first diluted with water. The ratio water/bottom residue is normally chosen from about 0.5:1 to 10:1, preferably from 1:1 to 4:1. If the salt content does not lie on an acceptable level after the dilution, the necessary amount of salt is added. Then the mixture is heated until a transparent solution is obtained, whereupon it is slowly chilled while it is stirred. The chilling should be performed to a temperature considerably below room temperature, preferably near 0°C, to give the best yield of crystals. The crystals are washed, separated by filtering, centrifuging or a similar process and finally dried. If a further improved purity of the product is desired, the wet crystals are dissolved in water and recrystallized once. Before the recrystallization the solution can be treated with active coal. The crystals obtained at the first crystallization can be purified by distillation too.

At a too low salt content of the aqueous solution a drastic decrease of the yield of pure THMO crystals is obtained depending on a decrease of the crystal size of the product obtained. The product becomes difficult to filter and wash. Repeated recrystallizatons are necessary to give an acceptable purity.

If on the other hand the salt content lies on a too high level, two layers are obtained. One gets an organic phase containing the main part of all the organic components and an aqueous phase containing the main part of the salt. This effect makes it more difficult to crystallize pure THMO.

However, at a suitable salt content crystals having a reasonable size are obtained without difficulty. These crystals are easy to filter and wash. Moreover, the product gets an acceptable purity.

If the method is performed with a recrystallization of the THMO product obtained in the first step, the filtrate obtained when the recrystallized THMO product has been filtered off can be used instead of water at the dissolution of the bottom residue. In this way one achieves that less water is added to the process. Then the amount of water which has to be evaporated or withdrawn from the process is considerably decreased.

At the process according to the present invention the distillation residue is dissolved in water as mentioned above. It has namely been found that it is impossible to obtain pure crystals of THMO independent of the salt content, if organic solvents such as acetone, methyl ethyl ketone, methyl isobutyl ketone, n-butanol, isobutanol, methyl formate, methyl acetate, ethyl acetat, butyl acetate or dioxane are used. By using these solvents a mixed product of THMO and the linear formal of bis-trimethylolpropane is obtained owing to the similar solubility properties of the two products in said solvents. The formal of bis-trimethylolpropane has the formula

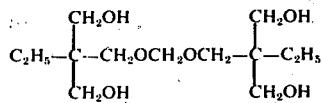

Said formal is more soluble than THMO in water. Thus, the separation problems present at the use of organic solvents are avoided according to the invention. This is a great advantage as the amount of formal in the distillation residue is often half as large as the amount of THMO or more.

The formal of bis-trimethylolpropane cannot be separated from THMO by distillation of the original bottom residue.

Thus, the method according to the invention is superior to other available methods for recovery of THMO from the distillation residue. The invention will be explained more in detail in connection with the embodiment examples given below.

EXAMPLE 1

Trimethylolpropane was produced in a way known in the art by reacting n-butyraldehyde and formaldehyde in an aqueous solution in the presence of sodium hydroxide. The solution obtained was evaporated to dryness. Precipitated sodium formate was filtered off and crude trimethylolpropane was obtained as a filtrate. Salt was removed by passing the product through an ion exchanger equipment. After evaporation of the water, the product was vacuum distilled at a pressure of about 10 mm Hg. Pure trimethylolpropane was obtained as a distillate. A bottom residue having the following composition was obtained:

| | | |
|---|---|---|
| Trimethylolpropane | 15.4 | % |
| THMO | 50.3 | % |
| Other organic by-products[1] | 34.1 | % |
| Sodium formate | 0.15 | % |

[1]Mainly cyclic and linear formals of trimethylolpropane and THMO.

This product is called bottom residue A below.

EXAMPLE 2

Trimethylolpropane was produced in a way known in the art by reacting n-butyraldehyde and formaldehyde in an aqueous solution in the presence of sodium hydroxide. The solution obtained was evaporated to dryness. The evaporation residue was dissolved in methyl isobutyl ketone. Precipitated sodium formate was filtered off. The solvent was distilled off, whereupon the remaining crude trimethylolpropane was distilled in a thin layer evaporator. A bottom residue having the following composition was obtained:

| | |
|---|---|
| Trimethylolpropane | 35.0 % |
| THMO | 35.4 % |
| Other organic by-products | 25.8 % |
| Sodium formate | 3.8 % |

This product is called bottom residue B below.

EXAMPLE 3

1.0 kg of bottom residue A was dissolved in 2.0 kg of water at 40°C. The solution was chilled slowly to 20°C while it was stirred. Grafting was brought about by using 10 g THMO crystals. The solution was chilled to 0°C while it was stirred continuously. The precipitate was filtered with difficulty in a small centrifuge and then it was washed with 2000 g of water. The precipitate had a dark brown color and contained a large amount of liquid which dissolved the precipitate when the temperature was raised for drying purposes. The dried product had a THMO content of 87 %.

EXAMPLE 4

10.0 kg of bottom residue A were dissolved in 20.0 kg of water at 40°C. 2.0 kg of sodium formate were added. The solution was chilled slowly to 20°C while it was stirred. Grafting was brought about by using 100 g of THMO crystals. The solution was chilled to 0°C while it was stirred continuously. The precipitated crystals were filtered off, washed with 4000 g of ice-cooled water and finally dried. 3870 g of THMO crystals were obtained having a melting point of 109° – 111°C, a THMO content of 98 % and an ash content of 0.02 %.

EXAMPLE 5

10.0 kg of bottom residue B were dissolved in 20 kg of water at 40°C. 1.5 kg of sodium formate were added. The solution was chilled slowly to 20°C while it was stirred. 100 g of THMO grafting crystals were added. The solution was chilled to 0°C while it was stirred continuously. The precipitated crystals were filtered off, washed with 4000 g of ice-cooled water and finally dried. 3030 g of THMO crystals were obtained having a melting point of 109° – 111°C, a THMO content of 97 % and an ash content of 0.03 %.

EXAMPLE 6

4520 g of the THMO product obtained according to example 4 were dissolved in 20.0 kg of water. The mixture was heated to 95°C and 200 g of active coal were added. The mixture was kept at 95°C for 1 hour while it was stirred, whereupon the coal was filtered off. Then the mixture was chilled slowly while it was stirred. The crystals were filtered off, washed with 9000 g of ice-cooled water and finally dried. 3920 g of THMO crystals were obtained having a melting point of 111° – 112°C, a THMO content of 97 % and an ash content being less than 0.01 %. As a filtrate a diluted solution was obtained, mainly consisting of THMO in water.

EXAMPLE 7

The process according to example 4 was repeated. However, instead of water the filtrate obtained in the process described in example 6 was used as a solvent. After crystallization, filtration, washing and drying, 4190 g of THMO crystals were obtained having a melting point of 109° – 111°C, a THMO content of 97 % and an ash content of 0.03 %. THMO has many fields of application. Among other things it can be used as a cross-linking agent at the production of alkyd resins. The compound can also be used for polyurethane resins and at the production of unsaturated and saturated polyester resins.

At the production of polyurethane resins the compound can be used as such. It can also be used after a reaction with an alkylene oxide or a dicarboxylic acid. If desired, the ether or ester respectively obtained thereby can then be reacted with isocyanate to another suitable starting product for the production of polyurethanes. Also an adduct of THMO and isocyanate can be used at the production of polyurethanes.

After a reaction with fatty acids THMO can be used as a lubricant for working of metal or for fast-moving turbine engines.

A reaction product of alkylene oxide and THMO can be used in another kind of hydraulic or lubricating oils.

THMO can as such or after an esterification be used as a coating material for pigment.

Esters of THMO with unsaturated polymerizable carboxylic acids can be used as cross-linking agents.

THMO can be available as an ester of phosphorous compounds, for example a phosphite ester, or as an ester of nitric acid. The last-mentioned kind of ester can be used as an explosive.

THMO can be used as a so-called synergistical additive to stabilizers, such as those of Ca/Zn and Ba/Cd type.

Esters of THMO can also be used as plasticizers, ester gums and as components in epoxy resins.

Allyl ethers and thioglycol esters of THMO can also be produced. Said compounds can be used for the same fields of application as the corresponding derivatives of adjacent polyalcohols.

Partial esters of THMO, for example dilaurate, can be used as antistatic agents and emulsifying agents.

Halogen containing esters or ethers of THMO can be used as fire retardants.

The present invention is not restricted to the embodiment examples shown as these can be modified in different ways within the scope of the invention.

I claim:

1. In a method for recovering pure 3,3,7,7-tetrahydroxymethyl-5-oxanonane from the bottom residue obtained in the production of trimethylolpropane from n-butyraldehyde and formaldehyde in the presence of an alkaline catalyst, said residue containing sodium formate, the improvement comprising mixing the residue with water in a ratio of from 0.5 to 10 parts water per part of residue, stirring the diluted residue until an aqueous solution is obtained, and cooling the solution to a temperature substantially below room temperature to precipitate pure crystals of 3,3,7,7-tetrahydroxymethyl-5-oxanonane, said diluted residue containing from 1 to 20 percent sodium formate calculated on the weight of the whole solution.

2. The method of claim 1 wherein the sodium formate is from 2 to 10 percent by weight.

* * * * *